(12) United States Patent
Ruan (10) Patent No.: US 12,106,830 B2
(45) Date of Patent: Oct. 1, 2024

(54) SKIN CARE PRODUCT FORMULATION DEVELOPMENT METHOD AND SYSTEM

(71) Applicant: SHENZHEN YUANGUANGZHOU TECHNOLOGY CO., LTD., Guangdong (CN)

(72) Inventor: Jing Ruan, Guangdong (CN)

(73) Assignee: SHENZHEN YUANGUANGZHOU TECHNOLOGY CO., LTD., Guangdong (CN)

(*) Notice: Subject to any disclaimer, the term of this patent is extended or adjusted under 35 U.S.C. 154(b) by 565 days.

(21) Appl. No.: 17/298,207

(22) PCT Filed: Feb. 11, 2020

(86) PCT No.: PCT/CN2020/074717
§ 371 (c)(1),
(2) Date: May 28, 2021

(87) PCT Pub. No.: WO2021/068440
PCT Pub. Date: Apr. 15, 2021

(65) Prior Publication Data
US 2022/0093218 A1    Mar. 24, 2022

(30) Foreign Application Priority Data
Oct. 9, 2019 (CN) .......................... 201910954588.7

(51) Int. Cl.
*G16C 20/70* (2019.01)
*G16C 20/30* (2019.01)

(52) U.S. Cl.
CPC ............. *G16C 20/70* (2019.02); *G16C 20/30* (2019.02)

(58) Field of Classification Search
CPC ........ G16C 20/70; G16C 60/00; G16C 20/30; A61K 8/18; A61Q 19/00
(Continued)

(56) References Cited

U.S. PATENT DOCUMENTS

2008/0014226 A1*  1/2008  Walker ................. A61K 8/18
                                                                 424/401
2008/0292734 A1*  11/2008  Hill ................... A61K 36/185
                                                                 424/738
(Continued)

FOREIGN PATENT DOCUMENTS

CN          107423347         12/2017
CN          107818124          3/2018
(Continued)

OTHER PUBLICATIONS

English translation of CN 109223580, Jan. 18, 2019. (Year: 2019).*
(Continued)

*Primary Examiner* — Michael P Nghiem
(74) *Attorney, Agent, or Firm* — Young Basile Hanlon & MacFarlane, P.C.

(57) ABSTRACT

Disclosed is a skin care product formulation development method and system. The method comprises: acquiring names and weights of new ingredients, searching formulations containing at least one of the new ingredients in a skin care product formulation database, and obtaining a plurality of candidate formulations; deleting the new ingredients contained in each of the candidate formulations to obtain a plurality of supplement formulations; clustering the plurality of supplement formulations based on ingredient correlations to obtain a plurality of cluster groups; calculating a correlation score of each cluster group to the deleted new ingredients respectively; and determining the cluster group with the highest correlation score, and generating a new skin care product formulation based on the cluster group with the highest correlation score.

11 Claims, 5 Drawing Sheets

(58) Field of Classification Search
USPC .......................................................... 702/32
See application file for complete search history.

(56) References Cited

U.S. PATENT DOCUMENTS

| | | | | |
|---|---|---|---|---|
| 2013/0177618 | A1* | 7/2013 | Schlessinger | A61K 31/573 |
| | | | | 424/401 |
| 2014/0018634 | A1* | 1/2014 | Baumann | G06Q 99/00 |
| | | | | 600/300 |
| 2017/0157031 | A1* | 6/2017 | Osborne | A61K 8/368 |
| 2018/0280905 | A1* | 10/2018 | Orsita | B01F 35/716 |
| 2019/0303377 | A1 | 10/2019 | Luo et al. | |

FOREIGN PATENT DOCUMENTS

| | | | | |
|---|---|---|---|---|
| CN | 109223580 A | * | 1/2019 | |
| CN | 110751989 | | 2/2020 | |
| WO | WO-2007087583 A2 | * | 8/2007 | .......... A61K 36/185 |

OTHER PUBLICATIONS

International Search Report for PCT/CN2020/074717 dated Jul. 8, 2020, 6 pages.
Written Opinion of the ISA for PCT/CN2020/074717 dated Jul. 8, 2020, 4 pages.

* cited by examiner

SKIN CARE PRODUCT FORMULATION DEVELOPMENT METHOD AND SYSTEM

CROSS-REFERENCE TO RELATED APPLICATIONS

This application is the U.S. national phase of International Application No. PCT/CN2020/074717 filed Feb. 11, 2020 which designated the U.S. and claims priority to CN 201910954588.7 filed Oct. 9, 2019, the entire contents of each of which are hereby incorporated by reference.

FIELD OF THE INVENTION

The present disclosure relates to the field of technology of computers, and in particular, to a skin care product formulation development method and system.

BACKGROUND

Figure 1:
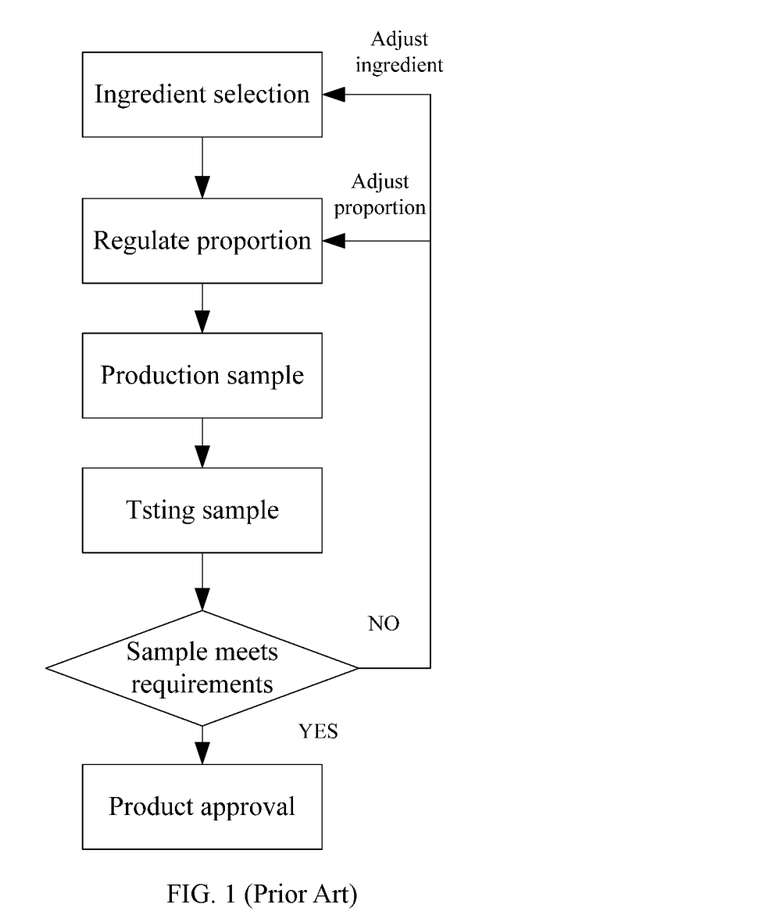
FIG. 1 is a schematic flow chart illustrating the development process of existing new skin care product formulations in the prior art.

In order to enable the characteristics of the new product such as efficacy, safety, comfort, texture, glossiness, oiliness, pH value and smell to reach the optimal form, links such as material selection, proportioning, debugging, proportioning adjustment and the like are required in the development process of the existing new skin care product formulation, and the process is shown in FIG. 1.

There are inefficiencies in the development of existing new skin care formulations. Formulators are familiar with the efficacy and toxicity of tens of thousands of ingredients, reasonable combination of ingredients, proportion of effective ingredients, oiliness, fragrance, pH value and the like of final products. The whole process of formulation is subjected to various iterations to complete the final product. The experience of the formulator determines the efficacy and quality of the final product.

Computer aided design methods are used in the process of formulation, mainly in the process of optimizing the proportion of ingredients. But from the selection of ingredients to the proportion of ingredients is a very complex process with optimization and selection required. With the increase of ingredients to be added, the collocation of the ingredients is increased, and the proportional relation becomes complex, and the restriction conditions are increased, and finding the optimal formulation becomes very difficult.

SUMMARY

Embodiments of the disclosure provide a formulation skin care product formulation development method and system that overcomes, or at least partially solves, the above-mentioned problems.

According to the first aspect, an embodiment of the disclosure provides a skin care product formulation development method, including: acquiring names and weights of new ingredients, searching formulations containing at least one of the new ingredients in a skin care product formulation database, and obtaining a plurality of candidate formulations; deleting the new ingredients contained in each of the candidate formulations to obtain a plurality of supplement formulations; clustering the plurality of supplement formulations based on ingredient correlations to obtain a plurality of cluster groups; calculating a correlation score of each cluster group to the deleted new ingredients respectively; and determining the cluster group with the highest correlation score, and generating a new skin care product formulation based on the cluster group with the highest correlation score.

Wherein, the step of clustering the plurality of supplement formulations based on the ingredient correlations to obtain a plurality of cluster groups specifically comprising: clustering the plurality of supplement formulations using a cluster algorithm such that at least two supplement formulations containing same ingredients form one cluster group; calculating cluster degrees of each cluster group based on the proportion of the same ingredients in respective formulations; and screening out the cluster group with the cluster degrees meeting a preset threshold value.

Wherein, the step of calculating the correlation score of each cluster group to the deleted new ingredients respectively, comprising: calculating the correlation degree of the candidate formulation corresponding to each supplement formulation in the current cluster group, and summing the correlation degrees to obtain the correlation score of the current cluster group to the deleted new ingredients; wherein, the correlation degree of the candidate formulation is calculated based on the content and weight calculation of each new ingredient in the candidate formulation.

Wherein, the step of correlation degree of the candidate formulation is calculated based on the content and weight calculation of each new ingredient in the candidate formulation, further comprising: the correlation degree of the candidate formulation is calculated based on the content and weight of each new ingredient in the candidate formulation, and the popularity of the candidate formulation in the market.

Wherein, the step of generating the new skin care product formulation based on the cluster group with the highest correlation score comprising: determining a candidate formulation corresponding to the cluster group with the highest correlation score; taking all new ingredients in the candidate formulation corresponding to the cluster group with the highest correlation score as one part of the final new skin care product formulation; taking the supplement formulation corresponding to the candidate formulation with the highest correlation degree in the candidate formulations corresponding to the cluster group with the highest correlation score as the other part of a final new skin care product formulation; or, determining the ingredients contained in all the supplement formulations in the cluster group with the highest correlation score as the other part of the final new skin care product formulation.

Wherein, the cluster algorithm is specifically realized based on a machine learning algorithm, and the machine learning algorithm comprises Bag of Words, KNN, Doc2Vec or tf-idf.

Wherein, the step of the correlation degree of the candidate formulation is calculated based on the content and weight of each new ingredients in the candidate formulation, and the popularity of the candidate formulation in the market, calculated using the following formulation:

the correlation degree of the candidate formulation=$f$ (the popularity of the candidate formulation in the market, $\Sigma_i$ content of new ingredient $i$ in the candidate formulation*weight), wherein, $f(\ )$ is a linear or nonlinear function.

According to the second aspect, an embodiment of the disclosure provides a skin care product formulation development system, including: a candidate formulation acquisition module, configured to acquire the names and the weights of the new ingredients, search formulations containing at least one of new ingredients in a skin care product formulation database, and obtain a plurality of candidate formulations; a supplement formulations obtaining module, configured to delete the new ingredients contained in each of the candidate formulations to obtain a plurality of supplement formulations; a cluster module, configured to cluster the plurality of supplement formulations based on ingredient correlations to obtain a plurality of cluster groups; a scoring module, configured to calculate a correlation score of each cluster group to the deleted new ingredients respectively; and a generation module, configured to determine the cluster group with the highest correlation score and generate a new skin care product formulation based on the cluster group with the highest correlation score.

According to the third aspect, an embodiment of the disclosure provides an electronic device comprising a memory, a processor and a computer program stored on the memory and executable on the processor, when executing the program, the processor performs the steps of the skin care product formulation development method provided in the first aspect are realized.

According to the fourth aspect, an embodiment of the disclosure provides a non-transitory computer readable storage medium, stored a computer program thereon, when the computer program is executed by a processor, implements the steps of the skin care product formulation development method provided in the first aspect are realized.

According to the skin care product formulation development method and system provided by the embodiment of the disclosure, on the basis of the existing skin care product formulation database, according to the ingredients to be added to match the existing formulation intelligently by utilizing a cluster algorithm, and the synthesis and adjustment are carried out on the basis of a plurality of related existing formulations, so that the new ingredients are blended, the optimization of the skin care product formulation development process is realized, and the optimal product formulation which is effective and meets the requirements can be efficiently generated.

BRIEF DESCRIPTION OF THE DRAWINGS

In order to more clearly illustrate the embodiments of the present disclosure or the technical solutions in the prior art, the drawings used in the embodiments or the description of the prior art will be briefly described below, and it is obvious that the drawings in the following description are some embodiments of the present disclosure, and other drawings can be obtained by those skilled in the art without creative efforts.

DETAILED DESCRIPTION OF THE EMBODIMENTS

In order to make the objects, technical solutions and advantages of the embodiments of the present disclosure clearer, the technical solutions in the embodiments of the present disclosure will be clearly and completely described below with reference to the drawings in the embodiments of the present disclosure, and it is obvious that the described embodiments are some, but not all embodiments of the present disclosure. All other embodiments, which can be obtained by a person skilled in the art without inventive step based on the embodiments of the present disclosure, are within the scope of protection of the present disclosure.

Figure 2:
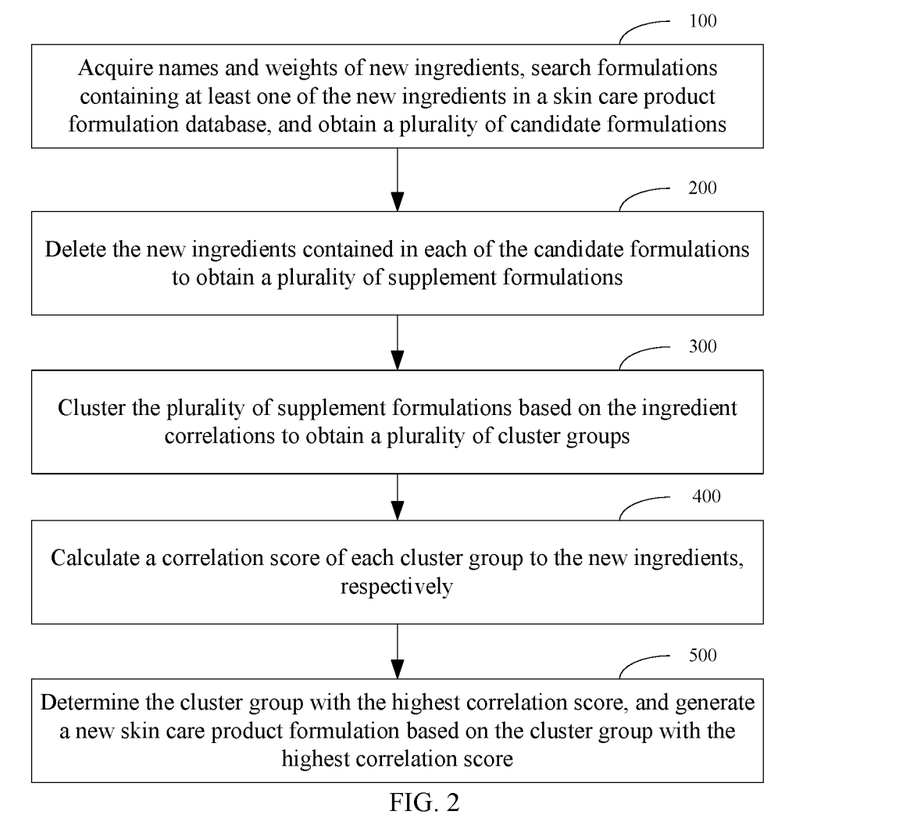
FIG. 2 is a schematic flow chart illustrating a skin care product formulation development method according to an embodiment of the present disclosure.

Referring to FIG. 2, FIG. 2 shows a schematic flow chart of a skin care product formulation development method according to an embodiment of the present disclosure, including step 100, step 200, and step 300.

In step 100, acquire names and weights of new ingredients, search formulations containing at least one of the new ingredients in a skin care product formulation database, and obtain a plurality of candidate formulations.

Specifically, the user inputs the expected ingredients to contained in new products (hereinafter referred to as new ingredients) and the weights of each ingredient, and the computer obtains the names and weights of the new ingredients input by the user, and then searches the existing skin care product formulation database for formulations containing at least one required new ingredients, which is called candidate formulations. For example, the new ingredients names A, B, and C are input by the user with weights of 2, 1.5, and 1, respectively. Then, a formulation containing at least any one of A, B, and C is searched for in the existing skin care formulation database as a candidate formulation. The following discussion will use the example of candidate formulation X, which contains 50% ingredient P, 20% ingredient A, 15% ingredient Q, 10% ingredient C and 5% ingredient R.

In step 200, delete the new ingredients contained in each of the candidate formulations to obtain a plurality of supplement formulations.

Specifically, the new ingredients contained in each candidate formulation are deleted, resulting in a plurality of supplement formulations. For example, delete the new ingredients contained in candidate formulation X, namely 20% ingredient A and 10% ingredient C, results in a supplement formulation X', X' containing 50% ingredient P, 15% ingredient Q and 5% ingredient R.

In step 300, cluster the plurality of supplement formulations based on the ingredient correlations to obtain a plurality of cluster groups.

Specifically, all supplement formulations are clustered, the purpose of which is to find the association between the individual supplement formulations, bring together the relevant supplement formulations and thus derive their commonality. For example, two formulations each contain ingredient A, and the two formulations can be clustered based on ingredient A. If two formulations do not have the same ingredient, the two formulations are not in the same group.

The embodiment of the disclosure clusters the plurality of supplement formulations based on the ingredient correlation, thereby realizing the automatic presentation or recommendation of the supplement formulations. For example, there are 4 candidate formulations:

$P1=\{A,E,F,G\}$ $P2=\{B,E,G,K,L,M,N\}$ $P3=\{C,P,Q,R,S\}$ $P4=\{B,R,S,Y\}.$

The supplement formulations corresponding to the above 4 candidate formulations are:

$P1'=\{E,F,G\}$ $P2'=\{E,G,K,L,M,N\}$ $P3'=\{P,Q,R,S\}$ $P4'=\{R,S,Y\}.$

Since both P1' and P2' contain the ingredients E, G, a single cluster group is formed. Since both P3' and P4' contain the ingredients R and S, they form another cluster group.

Embodiments of the present disclosure utilize a machine learning based cluster model to enable cluster of multiple supplement formulations.

Figure 3:
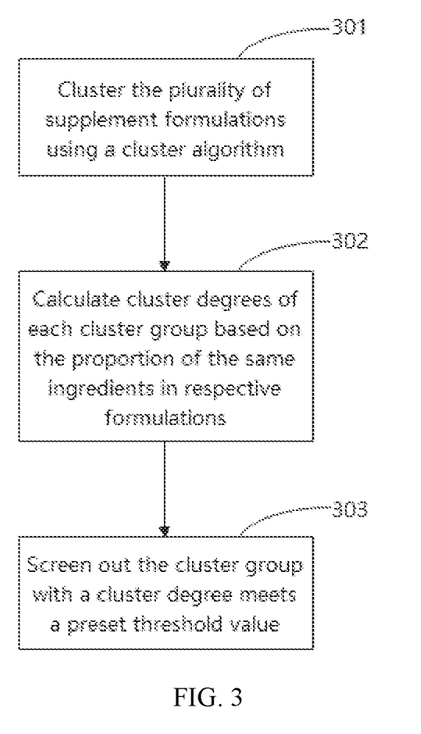
FIG. 3 is a schematic flow chart illustrating the specific steps of cluster the plurality of supplement formulations based on the ingredient correlations to obtain a plurality of cluster groups according to an embodiment of the present disclosure.

Further, the step 300 of cluster the plurality of supplement formulations based on the ingredient correlations to obtain a plurality of cluster groups includes step 301, step 302 and step 303.

In step 301, cluster the plurality of supplement formulations using a cluster algorithm such that at least two supplement formulations containing the same ingredients form one cluster group.

Specifically, the cluster algorithm is implemented based on a machine learning algorithm, finding similar supplement formulations by counting how many ingredients are the same between formulations, where the machine learning algorithms include but are not limited to, Bag of Words, k-near Neighbor algorithm (KNN), Doc2Vec or term frequency-inverse text frequency index (tf-idf). Herein, the realization principle of the Doc2Vec model or tf-idf model is to count the occurrence frequency of keywords in paragraphs or sentences, and clustering samples with close occurrence frequencies of keywords into a group.

It should be noted that, the embodiment of the present disclosure does not set any limit to the specific implementation of the cluster algorithm.

In step 302, calculate cluster degrees of each cluster group based on the proportion of the same ingredients in respective formulations.

Specifically, since some ingredients are often present in various formulations, large clusters are often generated in practice (i.e., one cluster contains many formulations). In order to reduce the occurrence of irrelevant formulations in the same clusters group, the embodiment of the disclosure proposes to eliminate irrelevant clusters by using the cluster degree.

The cluster degree between two formulations is defined as the sum of the proportion of the same ingredients in the respective formulations. Following the above example, P1' and P2' are clustered via ingredients E, G. The proportion of E and G in P1' and P2' is 10%, 20%, 10% and 30% respectively. Thus, the cluster degree of P1' and P2' is 10%+20%+10%+30%=70%.

Calculating the cluster degree of each cluster group is to calculate the cluster degree between the supplement formulations in the cluster group.

In step 303, screen out the cluster group with a cluster degree meets a preset threshold value.

In specific implementation, the size of the cluster group can be adjusted by adjusting a preset threshold value of the cluster degree. It will be understood that formulations with a cluster degree less than a predetermined threshold value cannot be placed in the same cluster group. A cluster group having a cluster degree that meets a predetermined threshold value means that the cluster degree between any two supplement formulations in the cluster group is greater than or equal to the predetermined threshold value.

In step 400, calculate a correlation score of each cluster group to the deleted new ingredients, respectively.

Specifically, in the embodiment of the present disclosure, each cluster group is scored according to the correlation with the deleted new ingredients. The correlation score of each cluster group to the new component is obtained from the correlation of the candidate formulation to which the supplement formulation in each cluster group corresponds.

Further, the step of calculate the correlation score of each cluster group to the new component includes:

calculating the correlation degree of the candidate formulation corresponding to each supplement formulation in the current cluster group, and summing the correlation degrees to obtain the correlation score of the current cluster group to the deleted new ingredients.

For example, if an cluster group has X', Y', Z' three supplement formulations, and the correlation degrees of the candidate formulations X, Y, and Z corresponding to each supplement formulation are calculated to be 90%, 100%, and 110%, respectively, then the correlation score of the cluster group to the deleted new ingredients is 90%+100%+110%=3.

In one embodiment, the correlation degree of a candidate formulation is calculated based on the content and weight of each of the new ingredients in the candidate formulation.

Specifically, the correlation degree of a candidate formulation is the sum of the contents and weights of the deleted new ingredients contained in the candidate formulation.

Namely that the correlation degree of a candidate formulation=$\Sigma_i$ content of new ingredient $i$ in the candidate formulation weight).

For example, for candidate formulation X, according to the contents and weights of ingredient A and ingredient C contained in X, then the correlation degree of candidate formulation X is 2*20%+1*10%=0.5.

Optionally, if there is a market popularity indicator, adjust the correlation degree of the formulation according to the popularity indicator of the formulation in the market.

In one embodiment, the correlation degree of the candidate formulation is calculated based on the content and weight of each new ingredient in the candidate formulation and the popularity of the candidate formulation in the market.

Specifically, the correlation degree of the candidate formulation is calculated based on the content and weight of each new ingredient in the candidate formulation and the popularity of the candidate formulation in the market, and by using the following formula to calculated:

the correlation degree of the candidate formulation=$f$ (the popularity of the candidate formulation in the market, content of new ingredient $i$ in the candidate formulation*weight)

wherein, f( ) is a linear or nonlinear function.

For example, if the product corresponding to the candidate formulation X has a score of 3 on the market, then the adjusted correlation is 0.5×3=1.5, and in this case, f( ) is a multiplication operation, which is a simple linear operation.

f( ) may be more complex non-linear functions. For example, the nonlinear transformation may be performed according to the width of the score interval. The scoring summary of general users are mostly distributed in the middle (2-3 points), and the two ends are small(1 point or 4 points). In specific implementation, nonlinear transformation can be performed according to the characteristic, and the adjusted weight is changed into smooth.

In step 500, determine the cluster group with the highest correlation score, and generate a new skin care product formulation based on the cluster group with the highest correlation score.

Specifically, after the correlation score of each cluster group is calculated, the cluster group with the highest correlation score is selected to generate a new skin care product formulation.

Figure 4:
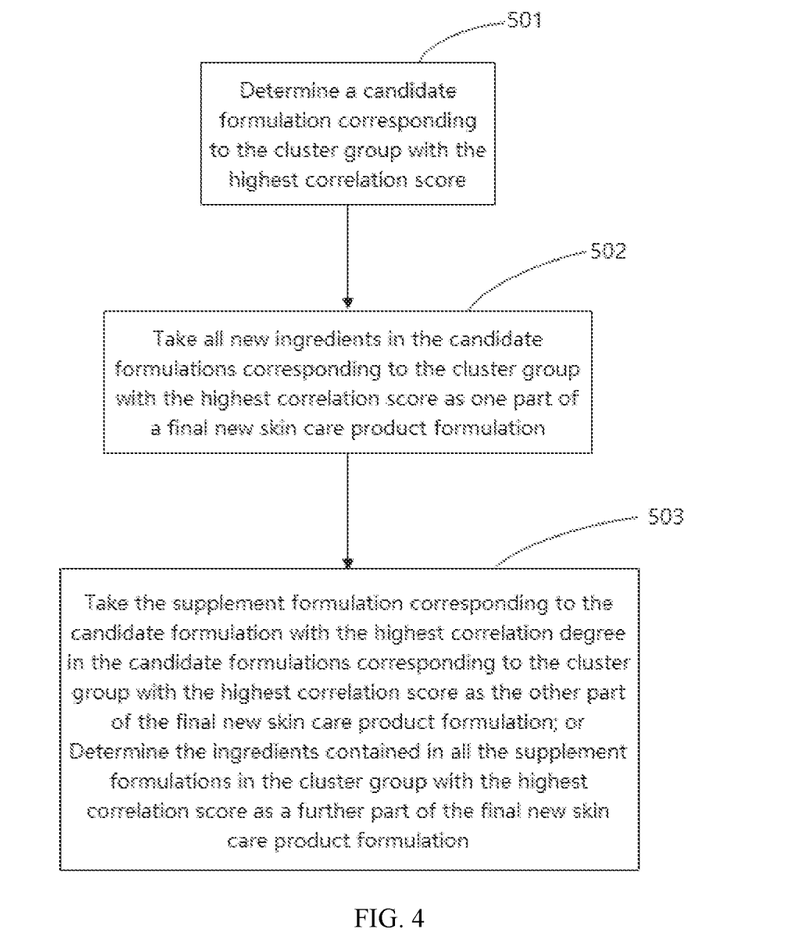
FIG. 4 is a schematic flow chart illustrating the specific steps of generate the new skin care product formulation based on the cluster group with the highest correlation score according to an embodiment of the present disclosure.

Further, the step 500 of generate the new skin care product formulation based on the cluster group with the highest correlation score includes step 501, step 502, and step 503.

In step 501, determine a candidate formulation corresponding to the cluster group with the highest correlation score.

Specifically, the candidate formulations corresponding to each supplement formulations in the cluster group with the highest correlation score is determined.

For example, the cluster group with the highest correlation score is {P1', P2'}, wherein, $P1'=\{E,F,G\}$ $P2'=\{E,G,K,L,M,N\}$.

The corresponding candidate formulation is:

$P1=\{A,E,F,G\}$, wherein the content of $A$ is 50% and the correlation degree is 2*50%=1;

$P2=\{B,E,G,K,L,M,N\}$, wherein the content of $B$ is 30%, and the correlation degree is 1.5*30%=0.45.

In step 502, take all new ingredients in the candidate formulations corresponding to the cluster group with the highest correlation score as one part of a final new skin care product formulation.

Following the above example, where P1 contains new ingredient A and P2 contains new ingredient B, the final new skin care product formulation will contain both A and B.

In step 503, take the supplement formulation corresponding to the candidate formulation with the highest correlation degree in the candidate formulations corresponding to the cluster group with the highest correlation score as the other part of the final new skin care product formulation; or, determine the ingredients contained in all the supplement formulations in the cluster group with the highest correlation score as a further part of the final new skin care product formulation.

Specifically, still following the above example, due to the correlation degree of P1 is big, then take the ingredients contained in supplement formulation P1' of P1 as the other part of the final new skin care product formulation, i.e. the final new skin care product formulation contained: A, B, E, F, G.

For another implementation, having the same ingredients contained in all of the supplement formulations in the cluster group with highest correlation score as part of the final new skin care formulation. Following the above example, where P1' and P2' contained the same ingredients as E and G, then the final new skin care product formulation contained: A, B, E, G.

According to the skin care product formulation development method provided by the embodiment of the disclosure, on the basis of the existing skin care product formulation database, according to the ingredients to be added to match the existing formulation intelligently by utilizing a cluster algorithm, and the synthesis and adjustment are carried out on the basis of a plurality of related existing formulations, so that the new ingredients are blended, the optimization of the skin care product formulation development process is realized, and the optimal product formulation which is effective and meets the requirements can be efficiently generated.

Figure 5:
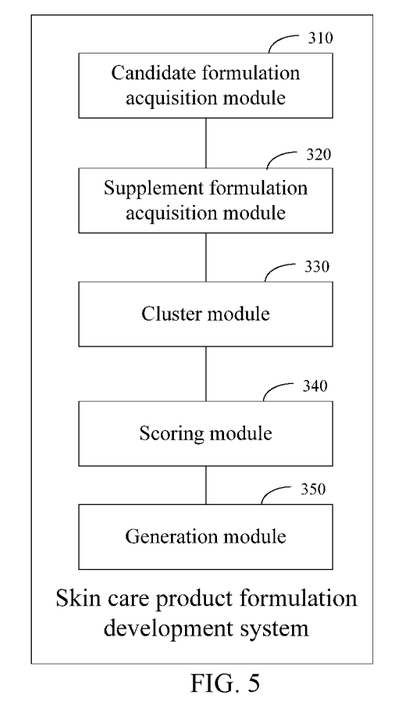
FIG. 5 is a schematic structural diagram illustrating a skin care product formulation development system according to an embodiment of the present disclosure.

Referring to FIG. 5, FIG. 5 shows a schematic structural diagram of a skin care product formulation development system according to an embodiment of the present disclosure, including: a candidate formulation acquisition module 310, a supplement formulation acquisition module 320, a cluster module 330, a scoring module 340, and a generation module 350.

The candidate formulation obtaining module 310 is configured to acquire names and weights of new ingredients, search formulations containing at least one of new ingredients in a skin care product formulation database, and obtain a plurality of candidate formulations.

Specifically, the user inputs the expected ingredients to contained in new products (hereinafter referred to as new ingredients) and the weights of each ingredients, and candidate formulation obtaining module 310 obtains the names and weights of the new ingredients input by the user, and then searches the existing skin care product formulation database for a formulation containing at least one required new ingredients, which is called a candidate formulation. For example, the new ingredients names A, B, and C are input by the user with weights of 2, 1.5, and 1, respectively. Then, a formulation containing at least any one of A, B, and C is searched for in the existing skin care formulation database as a candidate formulation. The following discussion will use the example of candidate formulation X, which contains 50% ingredient P, 20% ingredient A, 15% ingredient Q, 10% ingredient C and 5% ingredient R.

The supplement formulations obtaining module 320 is configured to delete the new ingredients contained in each of the candidate formulations to obtain a plurality of supplement formulations.

Specifically, the supplement recipe acquisition module 320 deletes the new ingredients contained in each candidate formulation, to form a plurality of supplement formulations. For example, delete the new ingredients contained in candidate formulation X, namely 20% ingredient A and 10% ingredient C, results in a supplement formulation X', X' containing 50% ingredient P, 15% ingredient Q and 5% ingredient R.

The cluster module 330 is configured to cluster the plurality of supplement formulations based on the ingredient correlations to obtain a plurality of cluster groups.

Specifically, the cluster module 330 clusters all of the supplement formulations, the purpose of which is to find the association between the individual supplement formulation, bring together the relevant supplement formulations and thus derive their commonality. For example, two formulations each contain ingredient A, and the two formulations can be clustered based on ingredient A. If two formulations do not have the same ingredients, the two formulations are not in the same group.

The cluster module 330 of the embodiment of the present disclosure clusters the plurality of supplement formulations based on the ingredient correlation, thereby realizing the automatic presentation or recommendation of the supplement formulations.

The scoring module 340 is configured to calculate a correlation score of each cluster group to the deleted new ingredients, respectively.

Specifically, the scoring module 340 adjusts the size of the cluster group by adjusting a preset threshold value of the cluster degree. It will be understood that formulations with a cluster degree less than a predetermined threshold value cannot be placed in the same cluster group. A cluster group having a cluster degree that meets a predetermined threshold value means that the cluster degree between any two supplement formulations in the cluster group is greater than or equal to the predetermined threshold value.

The generating module 350 is configured to determine the cluster group with the highest correlation score, and generate a new skin care product formulation based on the cluster group with the highest correlation score.

Specifically, the generation module 350 scores each cluster group according to a correlation with new ingredients. The correlation score of each cluster group to the new components is obtained from the correlation degree of the candidate formulations to which the supplement formulations in each cluster group corresponds.

According to the skin care product formulation development system provided by the embodiment of the disclosure, on the basis of the existing skin care product formulation database, according to the ingredients to be added to match the existing formulation intelligently by utilizing a cluster algorithm, and the synthesis and adjustment are carried out on the basis of a plurality of related existing formulations, so that the new ingredients are blended, the optimization of the skin care product formulation development process is realized, and the optimal product formulation which is effective and meets the requirements can be efficiently generated.

Figure 6:
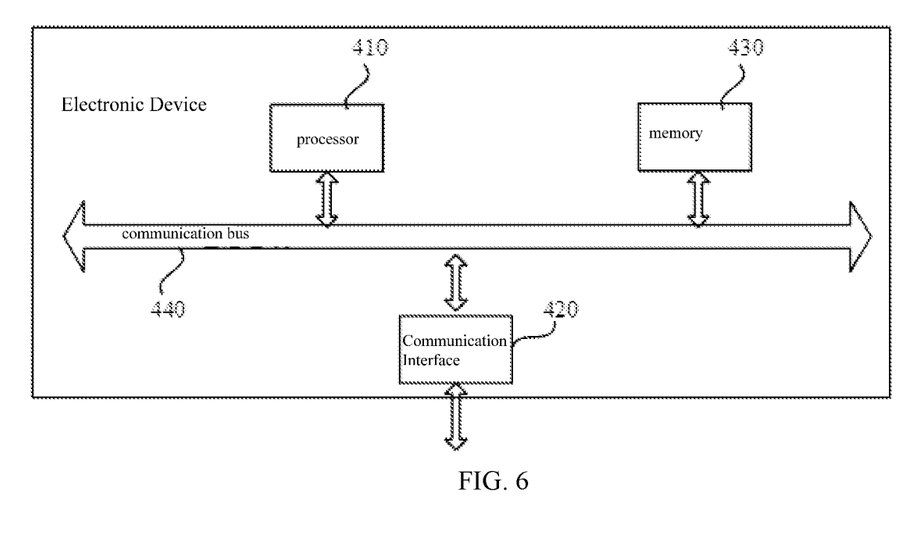
FIG. 6 is a schematic diagram illustrating the physical structure of an electronic device according to an embodiment of the present disclosure.

FIG. 6 is a schematic diagram illustrating the physical structure of an electronic device according to an embodiment of the present disclosure. As shown in FIG. 6, the electronic device may include: a processor 410, a Communication Interface 420, a memory 430 and a communication bus 440, wherein the processor 410, the Communication Interface 420 and the memory 430 are in communication with each other via the communication bus 440. The processor 410 may invoke a computer program stored on the memory 430 and executable on the processor 410 to perform the skin care formulation development method provided by the method embodiments described above, including, for example: acquiring names and weights of new ingredients, searching formulations containing at least one of the new ingredients in a skin care product formulation database, and obtaining a plurality of candidate formulations; deleting the new ingredients contained in each of the candidate formulations to obtain a plurality of supplement formulations; clustering the plurality of supplement formulations based on ingredient correlations to obtain a plurality of cluster groups; calculating a correlation score of each cluster group to the deleted new ingredients respectively; and determining the cluster group with the highest correlation score, and generating a new skin care product formulation based on the cluster group with the highest correlation score.

In addition, the logic instructions in the memory 430 can be implemented in the form of software functional units and stored in a computer readable storage medium when the logic instructions are sold or used as a stand-alone skin care product. Based on such understanding, the technical solutions of the embodiments of the present disclosure, which essentially or partly contribute to the prior art, may be embodied in the form of a software skin care product, which is stored in a storage medium and includes several instructions for causing a computer device (which may be a personal computer, a server, or a network device, etc.) to perform all or part of the steps of the methods described in the embodiments of the present disclosure. And the aforementioned storage medium includes: various media capable of storing program codes, such as U disk, removable hard disk, Read-Only Memory(ROM), Random Access Memory (RAM), magnetic disk or optical disk.

Embodiments of the present disclosure further provide a non-transitory computer readable storage medium, on which a computer program is stored, where the computer program, when executed by a processor, implements the steps of the skin care product formulation development method provided in the foregoing method embodiments, for example, the method includes: acquiring names and weights of new ingredients, searching formulations containing at least one of the new ingredients in a skin care product formulation database, and obtaining a plurality of candidate formulations; deleting the new ingredients contained in each of the candidate formulations to obtain a plurality of supplement formulations; clustering the plurality of supplement formulations based on ingredient correlations to obtain a plurality of cluster groups; calculating a correlation score of each cluster group to the deleted new ingredients respectively; and determining the cluster group with the highest correlation score, and generating a new skin care product formulation based on the cluster group with the highest correlation score.

The above-described embodiments of the apparatus are merely illustrative, and the units described as separate parts may or may not be physically separate, and parts displayed as units may or may not be physical units, may be located in one position, or may be distributed on multiple network units. Some or all of the modules may be selected according to actual needs to achieve the purpose of the solution of this embodiment. One of ordinary skill in the art can understand and implement it without inventive effort.

Through the above description of the embodiments, those skilled in the art will clearly understand that each embodiment may be implemented by software plus a necessary general hardware platform, and may also be implemented by hardware. Based on such understanding, the technical solutions in essence or contributing to the prior art may be embodied in the form of a software skin care product, which may be stored in a computer readable storage medium, such as ROM/RAM, magnetic disk, optical disk, etc., and includes several instructions for causing a computer device (which may be a personal computer, a server, or a network device, etc.) to execute the method according to the various embodiments or some parts of the embodiments.

Finally, it should be noted that: the above examples are only intended to illustrate the technical solution of the present disclosure, and not to limit it; although the present disclosure has been described in detail with reference to the foregoing embodiments, it should be understood by those of ordinary skill in the art that: the technical solutions described in the foregoing embodiments may still be modified, or some technical features may be equivalently replaced; and such modifications or substitutions do not depart from the spirit and scope of the corresponding technical solutions of the embodiments of the present disclosure.

The invention claimed is:

1. A skin care product formulation development method, comprising:
acquiring names and weights of new ingredients, searching formulations containing at least one of the new ingredients in a skin care product formulation database, and obtaining a plurality of candidate formulations;
deleting the new ingredients contained in each of the candidate formulations to obtain a plurality of supplement formulations;
clustering the plurality of supplement formulations based on ingredient correlations to obtain a plurality of cluster groups;
calculating a correlation score of each cluster group to the new ingredients that need to be added respectively;
determining a cluster group with a highest correlation score,
generating a new skin care product formulation based on the cluster group with the highest correlation score, and
producing a skin care product based on the new skin care product formulation;
wherein clustering the plurality of supplement formulations based on the ingredient correlations comprises:
clustering the plurality of supplement formulations using a cluster algorithm based on a machine learning algorithm such that at least two supplement formulations containing same ingredients form one cluster group;
calculating cluster degrees of each cluster group based on the proportion of the same ingredients in respective formulations; and
screening out a cluster group with cluster degrees meeting a threshold value.

2. The skin care product formulation development method according to claim 1, wherein calculating the correlation score of each cluster group to the deleted new ingredients comprises:
calculating a correlation degree of a candidate formulation corresponding to each supplement formulation in a current cluster group, and summing the correlation degree of the candidate formulation to obtain the correlation score of the current cluster group to the new ingredients that need to be added;
wherein,
the correlation degree of the candidate formulation is calculated based on content and weight calculation of each new ingredient in the candidate formulation.

3. The skin care product formulation development method according to claim 2, wherein calculating the correlation degree of the candidate formulation based on the content and weight calculation of each new ingredient in the candidate formulation further comprises:
calculating the correlation degree of the candidate formulation based on the content and weight of each new ingredient in the candidate formulation, and popularity of the candidate formulation in the market.

4. The skin care product formulation development method according to claim 3, wherein the correlation degree of the candidate formulation is calculated based on the content and weight of each new ingredients in the candidate formulation, and the popularity of the candidate formulation in the market by using the following formulation:

the correlation degree of the candidate formulation=$f$(the popularity of the candidate formulation in the market, $\Sigma_i$ content of new ingredient $i$ in the candidate formulation*weight), wherein, $f(\ )$ is a linear or nonlinear function.

5. The skin care product formulation development method according to claim 1, wherein generating the new skin care product formulation based on the cluster group with the highest correlation score comprises:
determining a candidate formulation corresponding to the cluster group with the highest correlation score;
taking the deleted new ingredients that need to be added in the candidate formulation corresponding to the cluster group with the highest correlation score as one part of a final new skin care product formulation;
taking supplement formulation corresponding to the candidate formulation with the highest correlation degree in the candidate formulations corresponding to the cluster group with the highest correlation score as an other part of a final new skin care product formulation; or
determining the ingredients contained in the supplement formulations in the cluster group with the highest correlation score as the other part of the final new skin care product formulation.

6. The skin care product formulation development method according to claim 1, wherein the machine learning algorithm comprises any of Bag of Words, k-near neighbor (KNN), Doc2 Vec or term frequency-inverse text frequency index (tf-idf).

7. An electronic device comprising a memory, a processor and a computer program stored in the memory and executable by the processor, wherein, when executing the computer program, the processor performs the steps of the skin care product formulation development method according to claim 1.

8. The skin care product formulation development method according to claim 1, wherein
when two formulations, from the plurality of supplement formulations, both contain a first ingredient, the two formulations are clustered into a cluster group based on the first ingredient, and
when two formulations, from the plurality of supplement formulations, do not contain a same ingredient, the two formulations are not clustered in the cluster group.

9. The skin care product formulation development method according to claim 1, wherein the plurality of supplement formulations are clustered based on the ingredient correlations thereby enabling automatic presentation or recommendation of the supplement formulations.

10. A skin care product formulation development system, comprising:
a processor; and
a memory configured to store computer readable instructions that, when executed by the processor, cause the processor to:
acquire names and weights of new ingredients, search formulations containing at least one of the new ingredients in a skin care product formulation database, and obtain a plurality of candidate formulations;
delete the new ingredients contained in each of the candidate formulations to obtain a plurality of supplement formulations;

cluster the plurality of supplement formulations based on ingredient correlations to obtain a plurality of cluster groups;

calculate a correlation score of each cluster group to the new ingredients that need to be added respectively;

determine a cluster group with a highest correlation score, generate a new skin care product formulation based on the cluster group with the highest correlation score, and produce a skin care product based on the new skin care product formulation;

wherein clustering the plurality of supplement formulations based on the ingredient correlations comprises:

clustering the plurality of supplement formulations using a cluster algorithm based on a machine learning algorithm such that at least two supplement formulations containing same ingredients form one cluster group;

calculating cluster degrees of each cluster group based on the proportion of the same ingredients in respective formulations; and screening out a cluster group with cluster degrees meeting a threshold value.

11. A non-transitory computer readable storage medium storing a computer program thereon, when the computer program is executed by a processor, the processor is caused to provide execution comprising:

acquiring names and weights of new ingredients, searching formulations containing at least one of the new ingredients in a skin care product formulation database, and obtaining a plurality of candidate formulations;

deleting the new ingredients contained in each of the candidate formulations to obtain a plurality of supplement formulations;

clustering the plurality of supplement formulations based on ingredient correlations to obtain a plurality of cluster groups;

calculating a correlation score of each cluster group to the new ingredients that need to be added respectively;

determining a cluster group with a highest correlation score, generating a new skin care product formulation based on the cluster group with the highest correlation score, and producing a skin care product based on the new skin care product formulation;

wherein clustering the plurality of supplement formulations based on the ingredient correlations comprises:

clustering the plurality of supplement formulations using a cluster algorithm based on a machine learning algorithm such that at least two supplement formulations containing same ingredients form one cluster group;

calculating cluster degrees of each cluster group based on the proportion of the same ingredients in respective formulations; and screening out a cluster group with cluster degrees meeting a threshold value.

* * * * *